US00PP12157P2

(12) United States Plant Patent
Slaughter et al.

(10) Patent No.: US PP12,157 P2
(45) Date of Patent: Oct. 23, 2001

(54) PEACH TREE NAMED 'BURPEACHTWO'

(75) Inventors: John K. Slaughter, Clovis; Timothy J. Gerdts, Kingsburg, both of CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 0 days.

(21) Appl. No.: 09/457,113

(22) Filed: Dec. 7, 1999

(51) Int. Cl.[7] ..... A01H 5/00
(52) U.S. Cl. ..... Plt./197

(58) Field of Search ..... Plt./197

*Primary Examiner*—Bruce R. Campell
*Assistant Examiner*—Susan B. McCormick
(74) *Attorney, Agent, or Firm*—Wells, St. John, Roberts, Gregory & Markin P.S.

(57) ABSTRACT

A new and distinct variety of peach tree denominated varietally as 'Burpeachtwo' and which is characterized as to novelty by a date of maturity for commercial harvesting and shipment of approximately August 1 to August 10 under the ecological conditions prevailing to the San Joaquin Valley of central California.

1 Drawing Sheet

BACKGROUND OF THE NEW VARIETY

The present invention relates to a new, novel and distinct variety of peach tree, which has the denominated varietally as 'Burpeachtwo'. The 'Burpeachtwo' Peach Tree produces an exceptionally high quality, clingstone peach which is mature for harvesting and shipment in late season. Another unique aspect of the 'Burpeachtwo' Peach Tree is that it yields a firm peach which exhibits very high eating quality as compared with the other peach varieties which mature at approximately the same time. In this regard, the 'Burpeachtwo' ripens approximately August 1$^{st}$ which is approximately 5–6 weeks before the ripening date of the 'Autumn Lady', the pollen parent; and approximately 7–9 days after the 'Summer Lady' peach tree, the seed parent.

ORIGIN

The present variety of peach tree resulted from an ongoing program of fruit and nut tree breeding. The purpose of this program is to improve the commercial quality of deciduous fruit and nut varieties and rootstocks by creating and releasing selections of prunus, malus and regia species. To this end, we make both controlled and hybrid crosses each year in order to produce seedling populations from which improved progenies are evaluated and selected. The seedling 'Burpeachtwo' was originated by us in 1993, and chosen from among a population of seedlings which were derived from a controlled cross of the Peach Tree 'Autumn Lady', (U.S. Plant Pat. No. 4,398) which was used as the pollen parent; and the 'Summer Lady' Peach Tree, (U.S. Plant Pat. No. 5,865), which was used as the seed parent. The resulting seeds from this controlled cross were planted in the spring of 1994. The new variety of peach tree was selected from among the seedlings then growing in the experimental orchards of the Assignee of the present application near the city of Fowler, Calif., County of Fresno in the San Joaquin Valley. The Peach Tree 'Burpeachtwo' was subsequently marked for observation and noted at that time as having exceptional characteristics. It has been subsequently and repeatedly evaluated during the 1995–1999 fruiting seasons. After the 1995 season, the Peach Tree 'Burpeachtwo' was selected for advanced evaluation and repropagation.

ASEXUAL REPRODUCTION

The new variety Peach Tree 'Burpeachtwo' was grafted into two different and existing 'Nemared' (non patented) peach rootstocks in February of 1996. The 'Nemared' rootstocks were planted in 1995. These rootstocks provide the means by which more information regarding the new variety could be derived. Scionwood from the original seedling of the Peach Tree, 'Burpeachtwo' was subsequently collected and grafted in the evaluation plot on the assignees experimental farm previously described. Fruit from the resulting propagation has been evaluated for each of the 1997, 1998 and 1999 fruiting seasons. These subsequent evaluations have clearly demonstrated that the repropagated trees are true to the characteristics of the original seedling in all observable aspects.

SUMMARY OF THE NEW VARIETY

The 'Burpeachtwo' Peach Tree is characterized as to novelty by producing late season fruit having a very high quality; which are very firm; and which also have an attractive exterior coloration. In this regard, the present variety of peach tree bears clingstone fruit which are ripe for commercial harvesting and shipment on approximately August 1 to August 10. These harvesting dates are approximately the same harvesting period as the common commercial freestone peach tree 'O'Henry' (U.S. Plant Pat. No. 2,964). The present variety of peach tree distinguishes itself from the 'O'Henry' Peach Tree however, by providing fruit having a bright exterior coloration, exceptional firmness, a clingstone trait and an extremely flavorful and juicy flesh quality. Further, the 'Burpeachtwo' Peach Tree distinguishes itself from the 'O'Henry' Peach Tree in that the 'O'Henry' peach has a background color that can vary from a greenish to yellow-green hue, while in contrast, the fruit produced by the 'Burpeachtwo' Peach Tree has a background color that is yellow-orange to orange in color.

BRIEF DESCRIPTION OF THE DRAWING

The accompanying drawing is a color photograph of a characteristic twig bearing typical leaves; several leaves showing both the dorsal and ventral coloration thereof; and several mature fruit showing their external coloration sufficiently matured for harvesting and shipment. Additionally one fruit of the subject variety is dissected in the equatorial or cheek plane to illustrate the flesh and stone characteristics.

DETAILED DESCRIPTION

Referring more specifically to the pomological details of the new and distinct variety of peach tree, the following has been observed under the ecological conditions prevailing at the assignee's orchards which are located at 6705 South Clovis Avenue near the town of Fowler, county of Fresno, state of California. All major color code designations are by reference to the R.H.S. Colour Chart (1995, Third Edition) provided by The Royal Horticultural Society of Great Britain.

Tree:

*Size.*—Generally — Average to above average as compared to other common peach cultivars.

*Productivity.*—Productive.

*Figure.*—The original seedling was trained in a central leader configuration with a moderate spread in the crown of the tree. The tree is considered upright to upright spreading in form.

*Height.*—The original seedling had a height dimension of 12.1 feet (3.6 m) after pruning at the end of the growing season in the winter of 1999.

*Width.*—The original seedling tree had a 6.8 feet width (2.07 m) at the end of the 1999 growing season under the prevailing ecological conditions then existing in the Central San Joaquin Valley.

*Current season growth.*—The current season growth for the new variety was approximately 3.1 to 3.5 feet (0.94–1.06 m).

*Regularity of bearing.*—Regular, and considered hardy under typical central San Joaquin Valley conditions.

Trunk:

*Diameter.*—Approximately 2.51 inches (63.5 mm) in diameter when measured at a distance of approximately six inches (15.24 cm) above the soil level, at the end of five consecutive growing seasons as measured in the winter of 1999.

*Bark texture.*—Considered moderately rough with numerous folds of papery scarf skin being present.

*Lenticels.*—Numerous flat, oval lenticels are present. The lenticels range in size from approximately 3.0 to 7.0 millimeters in width and from approximately 1 to 2 millimeters in height.

*Bark coloration.*—Variable, but it is generally considered to be a grey-brown (RHS Greyed-Orange Group 175 A).

Branches:

*Size.*—Considered medium for the variety.

*Diameter.*—Average as compared to other varieties. This is not distinctive of the variety.

*Surface texture.*—Average, and appearing furrowed on wood which is several years old.

*Crotch angels.*—Typically ranging from 45–58 degrees from horizontal. This characteristic is not distinctive of the tree due to cultural practices.

*Color of mature branches.*—Medium brown, (RHS Greyed Orange Group 172 B to 200 B).

*Current season shoots.*—Color — Light Green, (RHS Yellow Green Group 144 C), with some reddish-brown coloration appearing on the exposed shoots, (RHS Greyed Red Group 181 B). The color of new shoot tip is considered a bright and shiny green, (RHS Green Group 143 B).

*Current season shoots.*—Surface texture — Substantially glabrous.

*Internode length.*—Approximately 2.2 to 2.4 cm.

*Lenticels.*—Length — 3–4 millimeters.

*Lenticels.*—Width — 1–1.5 millimeters.

*Lenticels.*—Color — Greyed Orange Group (177D).

Leaves:

*Size.*—Considered average to small for the species. Leaf measurements have been taken from vigorous upright current season growth at mid-shoot.

*Leaf length.*—Approximately 160 to 178 millimeters.

*Leaf width.*—Approximately 40 to 45 millimeters.

*Leaf thickness.*—Approximately 1 to 2 millimeters.

*Leaf form.*—Lanceolate.

*Leaf tip form.*—Acuminate. The tip often appears flexed downwards and ventrally.

*Leaf base shape.*—Slightly oblique.

*Leaf color.*—Dark green, (RHS Green Group 135 C).

*Leaf texture.*—Smooth.

*Lower surface.*—Light green, (RHS Yellow Green Group 146 B).

*Veination.*—Pinnately net veined.

*Mid-vein.*—Color — Light yellow green, (RHS Yellow Green Group 150 D).

*Leaf margins.*—Form — Considered crenate, occasionally doubly crenate.

*Uniformity.*—Considered generally uniform.

*Leaf petioles.*—Size — Considered medium.

*Length.*—Approximately 6 to 10 millimeters.

*Diameter.*—Approximately 1.5 to 2 millimeters.

*Color.*—Pale green, (RHS Yellow Green Group 150 C).

*Leaf glands.*—Size — Approximately one to two millimeters in height and two to three millimeters in width.

*Numbers.*—Generally 2–3 per side, occasionally one per side.

*Type.*—Reniform.

*Color.*—Greenish brown, (RHS Grey Brown 199 C).

*Leaf stipules.*—Size — Medium for the variety.

*Number.*—2 stipules per leaf bud and up to 6 stipules per shoot tip.

*Length.*—Approximately 5 to 9 millimeters.

*Width.*—Approximately 1.0 millimeters wide.

*Form.*—Linear in form with a serrated margin.

*Color.*—Green (RHS Green Group 135A) when young but graduating to brown (RHS Greyed Orange Group 177A) with advancing senescence. The stipules are considered to be early deciduous.

Flowers:

*Flower buds.*—Generally — The floral buds are considered to be 21–24 mm in length, 14–17 mm in width, conic in form, and slightly appressed relative to the bearing shoot.

*Flower buds.*—Color — The bud scales are gray-brown, (approximately RHS Greyed Orange Group 177 C).

*Hardiness.*—The buds are considered hardy under typical central San Joaquin Valley climatic conditions.

*Blooming type.*—Considered average to slightly later than average in relation to other peach cultivars commonly growing in the central San Joaquin Valley. Date of first bloom — Feb. 28, 1998. Date of full bloom was March 4, in 1998.

*Bloom duration.*—Typically 10–12 days.
*Flower type.*—The variety is considered to be a showy type flower.
*Flower size.*—Flower diameter at full bloom is approximately 37 to 41 millimeters.
*Bloom quantity.*—Considered abundant.
*Flower bud frequency.*—Normally 1 to 2 buds appear per node, although 1 bud per node is more common.
*Petal size.*—Generally — Considered medium large for the species.
*Length.*—Approximately 18 to 20 millimeters.
*Width.*—Approximately 16 to 19 millimeters.
*Petal form.*—Broadly ovate.
*Petal count.*—Nearly always 5.
*Petal texture.*—Glaborous.
*Petal color.*—Light pink when young, (approximately RHS Red Purple Group 68 C), and darkening with advancing senescence to a medium pink, (RHS Red Purple Group 68 B). Lower portions of the petal are typically darker and exhibit a medium pink coloration (RHS Red-Purple Group 62A).
*Petal claw.*—Form — The claw is considered truncate in shape and has a medium size when compared to other similar varieties.
*Length.*—Approximately 1.5 to 2.1 millimeters.
*Width.*—Approximately 1 millimeter.
*Petal margins.*—Generally — Considered variable, from nearly smooth, to highly undulate.
*Petal apex.*—Generally — The petals apices appear slightly domed.
*Flower pedicel.*—Length — Considered medium-short, and having an average length of approximately 1.9 to 2.6 millimeters.
*Diameter.*—Approximately 2 millimeters.
*Color.*—Bright green, (RHS Yellow Green Group 144 D).
*Floral nectaries.*—Color — Dull, orange to an orange-gold color, (approximately RHS Greyed Orange Group 169 D). The color of the nectaries become more dull and slightly darker with advancing senescence.
*Calyx.*—Surface Texture — Generally glabrous.
*Color.*—A dull red, (approximately RHS Greyed Red Group 181 A).
*Sepals.*—Surface Texture — The surface of the sepals have a medium length, wooly, and gray colored pubescence. This color is not distinctive of the variety.
*Number.*—Generally 5 per flower.
*Size.*—Typically 4–5 mm wide and 5–6 mm in length, and ovate in form.
*Color.*—A dull red, (approximately RHS Greyed Purple Group 184 B).
*Anthers.*—Generally — 1.0 mm in width and 1.0–1.5 mm in length.
*Color.*—Red to reddish-orange dorsally, (approximately RHS Greyed Red Group 178 C).
*Pollen production.*—Pollen is abundant, and has a yellow-gold color, (approximately RHS Yellow Orange 19 A).
*Filaments.*—Size — Variable in length, approximately 14 to 16 millimeters.
*Color.*—White, (RHS White Group 155 D), and darkening with advanced maturity.
*Pistil.*—Generally — Average in size.
*Length.*—Approximately 15 to 17 millimeters, including the ovary.
*Color.*—Considered a very pale green when young, (approximately RHS Yellow Green Group 150 D).
*Surface texture.*—Pubescent.

Fruit:

*Maturity when described.*—The present variety of fruit is described, as it would be found in its firm ripe condition at full commercial maturity. In this regard, the fruit of the present variety was first picked on approximately Aug. 1, 1998. The date of last pick of the same fruit in 1998 was approximately August 10 under the ecological conditions prevailing in the San Joaquin Valley of central California.
*Size.*—Generally — Large, and considered moderately uniform.
*Fruit weight.*—Typically — 175 grams utilizing typical cultural practices employed in the Central San Joaquin Valley.
*Average cheek diameter.*—Approximately 80 to 82 millimeters.
*Average suture diameter.*—Approximately 73 to 77 millimeters.
*Average axial diameter.*—Approximately 78 to 80 millimeters.
*Fruit form.*—Generally — Oblate in its lateral aspect. The fruit is generally uniform in symmetry with a slightly oval form when viewed from the apical aspect.
*Fruit suture.*—Generally — The suture appears as a thin line which extends from the base to the apex, and appears slightly deeper, basally, within the stem well, and apically on both sides of the pistil point. No apparent callousing or stitching exists along the suture line.
*Suture.*—Color — The suture normally is the same color as the underlying blush color, both where the orange-yellow background, (RHS Yellow Orange Group 21 C) and the red orange color, (RHS Red Group 47) A), occur.
*Ventral surface.*—Form — Considered uniform.
*Stem cavity.*—Size — Considered moderate for the species.
*Width.*—Approximately 21–23 millimeters.
*Length.*—Approximately 33–35 millimeters.
*Depth.*—Approximately 11 to 12 millimeters.
*Form.*—Considered narrowly oval.
*Fruit base.*—Generally — Considered truncate in form, and uniform.
*Fruit apex.*—Generally — Considered depressed and usually recessed below the height of the apical shoulders and often oblique to the suture.
*Fruit stem.*—Generally — Considered medium in length, approximately 9 to 11 millimeters.
*Diameter.*—Approximately 3 to 4 millimeters.
*Color.*—Generally a pale yellow-green, (approximately RHS Yellow Green Group 145 B).
*Fruit skin.*—Generally — Considered medium or average in thickness.
*Surface texture.*—The variety has very light, short pubescence.
*Skin acidity.*—Considered neutral.
*Tenacious to flesh.*—Yes at commercial maturity.
*Tendency to crack.*—Not observed.
*Skin color.*—Generally — Variable, with approximately 70% to 90% of the fruit surface covered with an attractive red blush.
*Blush color.*—The blush color is generally more prevalent apically. This red blush color ranges from a dark red, (RHS Red Group 47 A) to an orange red, (RHS Red Group 33 B), with many degrees of shading and blending between these colorations.

*Skin ground color.*—This is generally present in variable percentages covering approximately 10% to 30% of the fruit's surface, and which is a Yellow-golden color, (RHS Yellow Orange Group 22 A to 20 D).

*Flesh color.*—Generally — Considered variable, from a yellow/orange, (RHS Yellow Orange Group 16A to 16 D), to reddish orange, (approximately RHS Red Group 45 B). This color can radiate into the flesh generally beginning at the exterior margin.

*Flesh fibers.*—Generally — Present, numerous, and light colored. These flesh fibers are present throughout the the flesh.

*Stone cavity.*—Color — Red, (approximately RHS Red Group 45 B), to a yellow orange, (approximately RHS Yellow Orange Group 18 B). With increasing maturity, occasional red flecks can appear randomly in the flesh. These flecks are more numerous nearer to the pit cavity than at the exterior margins.

*Flesh texture.*—Generally — The flesh is considered firm and fine at commercial maturity.

*Ripening.*—Generally — The fruit of the present variety ripens evenly.

*Flavor.*—Considered very sweet and having mild acidity. The flavor is considered both pleasant and balanced.

*Aroma.*—Pleasant and abundant.

*Eating quality.*—Generally — Considered very good to excellent and well above average when compared to other common varieties.

Stone:

*Attachment.*—Generally — The stone is considered a true clingstone at full commercial maturity.

*Stone size generally.*—Considered medium for the species.

*Length.*—Approximately 32 to 35 millimeters.

*Width.*—Approximately 28 to 30 millimeters.

*Diameter.*—Approximately 23 to 25 millimeters.

*Fibers.*—Generally — A few medium length fibers are attached along the entire surface area of the stone.

*Stone form.*—Generally — The stone is considered oval.

*Stone base.*—The stone base is somewhat oblique.

*Base angle.*—The base angle of the stone is variable, but most frequently is considered slightly oblique to the stone axis.

*Hilum.*—Generally — Considered medium in size, and relatively well defined. The hilum is approximately 5 to 7 millimeters long and approximately 3 to 4 millimeters wide.

*Form.*—Considered oval.

*Apex.*—Shape — The stone apex is raised and had a rounded tip.

*Stone shape.*—Considered Variable. The stone is normally unequal, although occasionally it may appear nearly equal.

*Stone surface.*—Surface Texture — Generally considered medium in roughness and exhibits substantial pitting laterally. Substantial grooving is apparent over the apical shoulders. Surface pitting is prominent generally, and occurs more frequently basally. Pits are generally more elongated in shape as opposed to typical pitting that is more cylindrically shaped.

*Ridges.*—Numerous fine ridges are present basally and converge towards the base of the stone.

*Ventral edge.*—Width — Considered medium, and having a dimension of approximately 5 to 7 millimeters at mid-suture with the wings being most prominent over the basal area.

*Dorsal edge.*—Full, heavily grooved and having jagged edges. The dorsal edge is moderately eroded over the apical shoulder.

*Stone color.*—The color of the dry stone is approximately a light to medium brown, (RHS Orange Red Group 34 B).

*Tendency to split.*—No splitting noted.

*Kernel.*—Form — Oval.

*Taste.*—Bitter.

*Viable.*—Yes; Average width — 10.9 mm; Average length — 19.7 mm.

*Use.*—The subject variety 'Burpeachtwo' Peach Tree is considered to be a peach tree which matures in the late season and which produces fruit which are very firm, have an attractive color, and which are commercially useful for both local and long distance markets.

*Keeping quality.*—Excellent. Fruit has in the past appeared to have stored well up to 18 days after harvest at a temperature of about 20° C.

*Resistance to insects and disease.*—No particular susceptibilities were noted.

*Shipping quality.*—Well above average.

Although this new variety of peach tree possesses the described characteristics noted above, as a result of the growing conditions prevailing in the central part of the San Joaquin Valley of Central California, it is to be understood that variations of the usual magnitude and characteristics incident to changes in growing conditions, fertilization, pruning and pest control are to be expected.

Having thus described and illustrated our new variety of peach tree what we claim as new and desire to secure by Plant Letters Patent is:

1. A new and distinct variety of peach tree substantially as illustrated and described and which is characterized as to novelty by producing an attractively colored clingstone peach, which is sufficiently matured for harvesting and shipment approximately August 1 to August 10 under the prevailing ecological conditions experienced in the San Joaquin Valley of Central California.

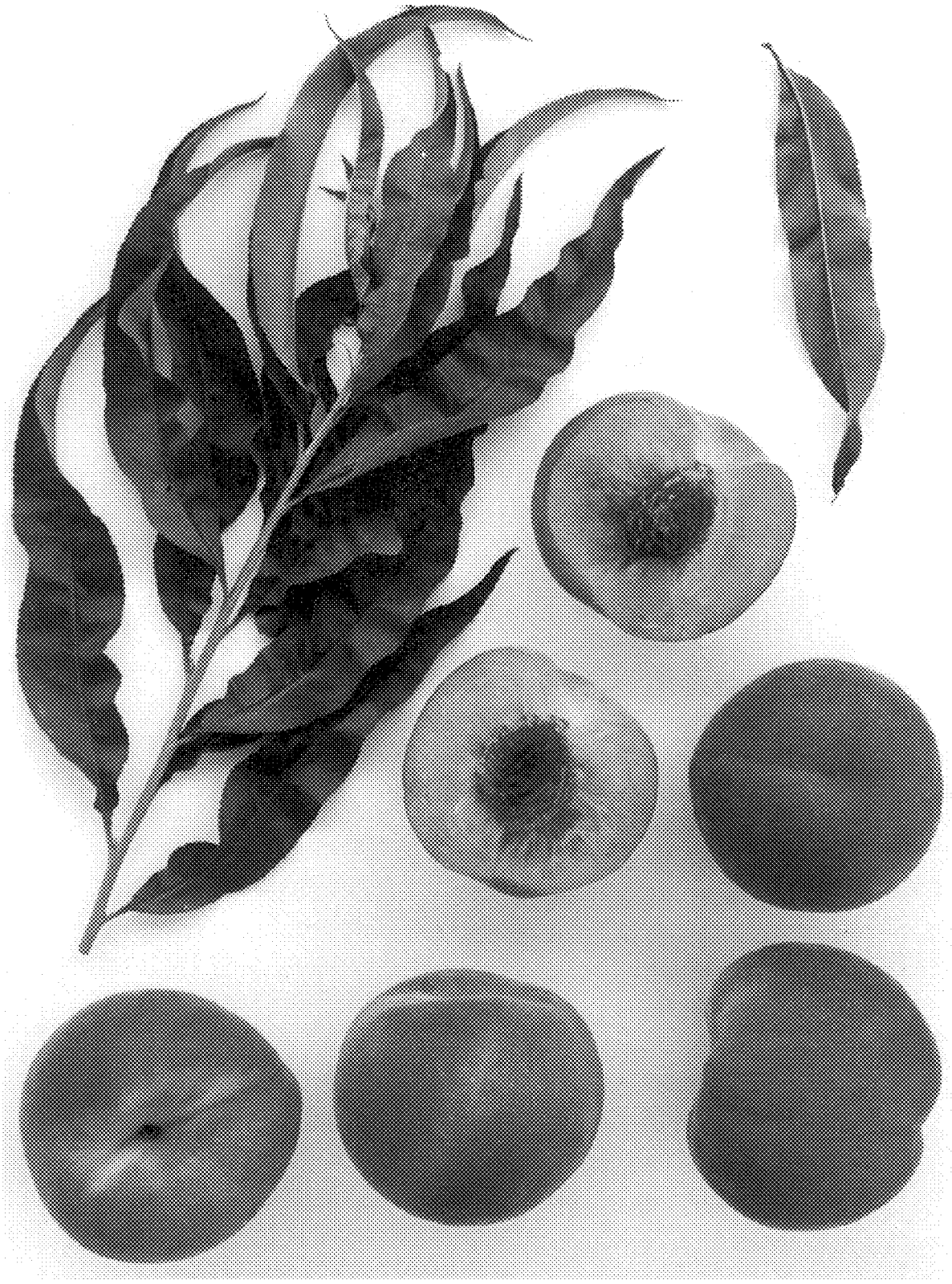

* * * * *